United States Patent
Yadav

[11] Patent Number: 6,096,071
[45] Date of Patent: Aug. 1, 2000

[54] OSTIAL STENT

[76] Inventor: Jay S. Yadav, 735 Aran Dr., Roswell, Ga. 30076

[21] Appl. No.: 09/048,447

[22] Filed: Mar. 26, 1998

Related U.S. Application Data

[60] Provisional application No. 60/041,699, Mar. 26, 1997.
[51] Int. Cl.[7] .............................. A61F 2/06; A61M 29/00
[52] U.S. Cl. .................... 623/1.15; 623/1.31; 623/12; 606/194; 606/195
[58] Field of Search ................... 623/1, 12; 606/215, 606/194, 195

[56] References Cited

U.S. PATENT DOCUMENTS

| | | |
|---|---|---|
| 4,265,244 | 5/1981 | Hill . |
| 4,994,071 | 2/1991 | MacGregor . |
| 5,064,435 | 11/1991 | Porter ........................................ 623/12 |
| 5,372,600 | 12/1994 | Beyar et al. .............................. 606/108 |
| 5,456,712 | 10/1995 | Maginot . |
| 5,466,242 | 11/1995 | Mori . |
| 5,607,444 | 3/1997 | Lam .......................................... 606/194 |
| 5,725,552 | 3/1998 | Kotula et al. ............................ 606/213 |
| 5,749,874 | 5/1998 | Schwartz ................................... 606/75 |
| 5,755,771 | 5/1998 | Penn et al. ................................... 623/1 |
| 5,876,448 | 3/1999 | Thompson et al. ........................ 623/12 |

Primary Examiner—David H. Willse
Assistant Examiner—Suzette Jackson
Attorney, Agent, or Firm—Cowan, Liebowitz & Latman, P.C.; William H. Dippert

[57] ABSTRACT

A stent for use in the treatment of stenosis of the ostium of tubular organs, more particularly, blood vessels comprising a multiplicity of flanges located at an end of a generally tubular stent body. The flanges permit the accurate positioning of the stent within the vessel, while presenting dislodgement of the stent.

14 Claims, 2 Drawing Sheets

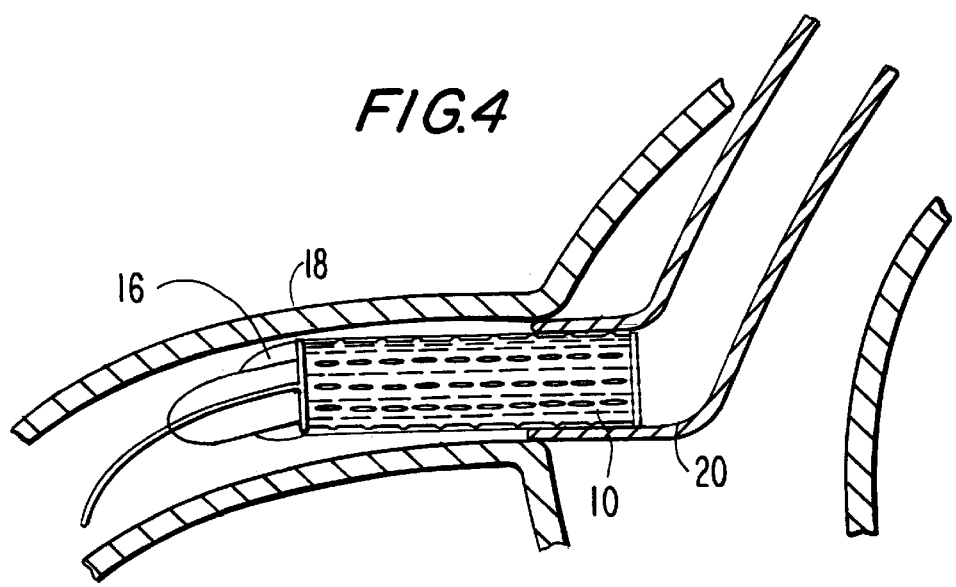
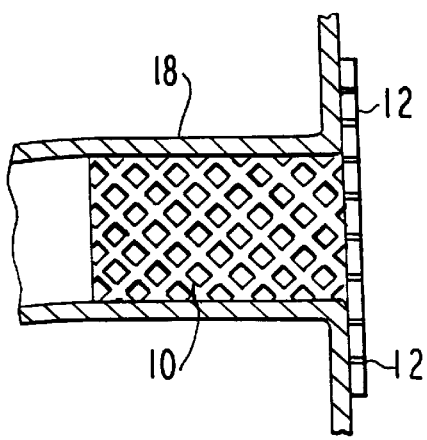
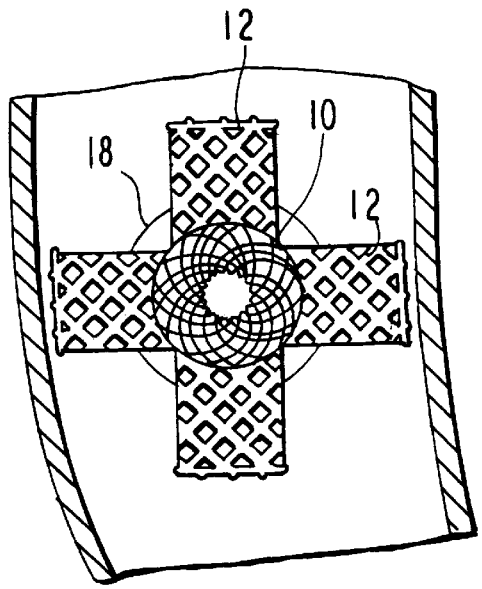

OSTIAL STENT

This application is based upon co-pending, commonly assigned U.S. provisional patent application Ser. No. 60/041,699, filed Mar. 26, 1997.

BACKGROUND OF THE INVENTION

The use of stents in blood vessels and other structures in the body has become a well established clinical procedure over the past decade. The equipment and techniques for deploying stents inside blood vessels and even at branch points are well established. There are, however, no effective devices or techniques available for stenting the ostium of blood vessels particularly arteries originating from the aorta. The tubular stents currently available are very difficult to position in the ostium of arteries; since the stent is either inserted too far leaving a critical portion of lesion uncovered, or the stent protrudes into the aorta. This problem occurs with balloon expandable, as well as self-expanding, stents, indeed with all stent designs currently available in the art.

A number of references are known. Hill, U.S. Pat. No. 4,265,244, discloses a flanged ostia tube for fitting within a stoma opening. MacGregor, U.S. Pat. No. 4,994,071, discloses a stent having an enlarged end (bifurcation). Maginot, U.S. Pat. No. 5,456,712, discloses a flanged stent member. Mori, U.S. Pat. No. 5,466,242, discloses a shape memory alloy stent where a portion of the stent flares in a funnel/conical shape to hold the stent in place. Lam, U.S. Pat. No. 5,607,144 discloses a specialized ostial stent for repairing vessels at bifurcations. However, none of the stents disclosed is believed to be as effective in the treatment of stenoses as the stent described below would be.

OBJECTS OF THE INVENTION

It is an object of the invention to provide for a novel stent for the treatment of stenoses at the ostium of tubular organs.

It is also an object of the invention to provide for a novel stent for the treatment of stenoses at the ostium of blood vessels.

It is another object of the invention to provide for a novel stent which permits the stent to be firmly positioned at the ostium of tubular organs.

Lastly, it is an object of the present invention to provide for a novel stent which comprises flanges to permit the accurate positioning of the stent, while at the same time preventing dislodgement of the stent from the position where it had been placed.

These and other objects of the invention will become apparent to one skilled in the art from the following more detailed disclosure of the invention.

SUMMARY OF THE INVENTION

The present invention is directed to a stent for use in the treatment of stenoses at the ostium of tubular organs and more particularly of blood vessels. The stent of the invention is comprised of an expandable tubular body and an end portion that is capable of flaring or being flared. To treat stenoses at the ostium, the ostial stent is placed within the organ with its flared members at the ostium, the flared members are flared or self-flared, and the remainder of the tubular body of the stent expands or is expanded.

The tubular body of the ostial stent is capable of radial expansion, either self-expansion or balloon expansion. The tubular body may comprise a geometric pattern or structural configuration that facilitates radial expansion. The tubular body must have sufficient radial strength that it retains its expanded cross-sectional area after expansion. Preferably the material of the tubular body will have a low metal-to-opening ratio.

The ostial stent of the invention comprises a generally tubular body in which one end comprises flaps or flaring members that are capable or extending away from the longitudinal axis of the tubular body. The tubular body and the flaring members may be comprised of the same or different materials. Preferably the tubular body and the flaring members are comprised of the same material. Also, although the tubular body of the flaring members could be comprised of two or more separate and distinct parts which have been attached, preferably they are formed from one continuous piece.

The flaring members are each capable of adopting an undeformed configuration that is substantially parallel to the longitudinal axis of the tubular body and a deformed configuration that is unparallel to, and at an angle from, said longitudinal axis. Preferably each flaring member will be capable of extending to a position approximately normal to the longitudinal axis. There will be from 3 to 8, preferably 4, flaring members.

Flaring members are attached to or, preferably, formed from the tubular body. For example, regularly-spaced incisions can be made into one end of the tubular body to create flaring members.

Placement of the ostial stent within an ostial stenosis comprises radial expansion of the tubular body and expansion and/or deformation of the flaring members. Radial expansion of the tubular body allows it to substantially conform to, and press against, the inner wall and stenosis of a tubular organ or vessel, thereby seating the ostial stent. The flaring members are deformed so that they substantially conform to the ostium of the tubular organ, thereby firmly securing the ostial stent at that site.

The ostial stent can be either balloon expandable or self-expanding. With regard to a balloon-expandable stent, the ostial stent is loaded onto the balloon of a balloon dilatation catheter with the flaring members unexpanded and substantially parallel to the longitudinal axis of the tubular body. The ostial stent is preferably placed upon the balloon with the flaring members on or adjacent to the proximal portion of the balloon and the tubular body loaded on the middle or distal portion of the balloon. There may be applications where the position will be reversed. The balloon and ostial stent are advanced to a desired site through a guiding catheter or a protective sheath. After the ostial stent is positioned at a desired site, the guiding catheter or protective sheath is withdrawn proximally to permit the flaring members to flare or expand at the ostium, and then the dilatation balloon is expanded to seat the stent.

Where the ostial stent is comprised of spring-like or similar material so as to be self-expanding, the ostial stent is secured to a delivery catheter in an unexpanded state or positioned in a delivery sheath and then advanced through a guiding catheter or protective sheath to a desired location. There are a number of known delivery systems for delivery of a self-expanding catheter. See, for example, U.S. Pat. Nos. 4,886,062, 4,913,141, 5,019,085, 5,147,370, 5,372,600, 5,507,768, 5,549,635, 5,607,467, 5,632,760, 5,643,278, and 5,669,932, each of which is incorporated herein by reference. Once the ostial stent is properly positioned, the stent is released from the delivery catheter or sheath.

It is also contemplated that radiopaque markers be formed in or attached to the ostial stent and placed so as to mark the joining line between the flaring portion and the tubular body. In addition, radiopaque markers could be placed to mark the circumferential location of each of the flaring members. Marking the ostial stent in this way facilitates proper placement and orientation of the ostial stent. The balloon catheter loaded with the ostial stent is advanced to the location of the diseased bifurcated vessel and by means of radiography, precise positioning of the ostial stent is achieved.

The tubular body and flaring members can be fabricated from a metal alloy, such as, preferably a shape-memory alloy, such as, for example, nickel-titanium alloy (nitinol), or another similar metallic or non-metallic material which possesses the characteristic of shape memory. Especially preferred is super-elastic nitinol. At a cold temperature, the tubular body would be in an unexpanded condition, and the flaring members would be unexpanded and substantially parallel to the longitudinal axis of the ostial stent. At an increased temperature, for example, body temperature, the tubular body expands or is expanded to seat at the ostium of a tubular organ, and the flaring members expand and deform to envelope the ostium. At a patient's normal body temperature, the ostial stent retains an expanded and deformed configuration, thereby sustaining a secure position at the ostium of the tubular organ.

BRIEF DESCRIPTION OF THE DRAWINGS

FIG. 4 depicts a schematic representation of the stent/retractable sheath shown positioned at the ostium of a vessel with the sheath about to be retracted;

FIG. 5 depicts a schematic representation of the stent shown in FIG. 4, in the fully extended position placed within the vessel and its ostium with the flared members of the stent positioned against the wall of the originating organ; and FIG. 6 depicts an end view of the stent shown in FIG. 5, shown in its fully extended position.

DETAILED DESCRIPTION OF THE INVENTION

The stent of the invention comprises a generally tubular body in which one end comprises integral flaps or flared members that are capable of extending from the longitudinal axis of the tubular body, i.e., the flared members. Prior to and during percutaneous insertion the flared members are substantially tubular; however, after a guiding and/or protective sheath is withdrawn distally, the flared members tend to move in a direction normal to the longitudinal axis.

The geometric configuration of the walls of the stent will vary for differing specific applications depending upon the requirements for rigidity, radial strength and flexibility.

It is contemplated that the stent of the invention will be collapsed inside a retractable sheath type delivery device with radiopaque markets at both ends of the stent as well as at the origin of the flanges so as to allow easy positioning. The stent is positioned in the vessel ostium using standard fluoroscopic and angiographic techniques. Subsequently, the sheath is retracted allowing the stent to assume its original shape. It is further contemplated that the stent would be fabricated in different sizes to allow stenting of a wide variety of vessels. Applications in which the stent of the invention would be used would include, but are not limited to, the ostia of the left main coronary artery, right coronary artery, innominate artery, left common carotid artery, subclavian artery, vertebral arteries, renal arteries, hepatic artery, and mesenteric arteries. Venous applications are also possible.

Figure 2A:
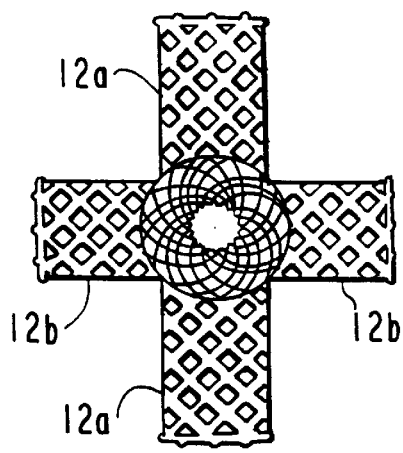
FIG. 2A depicts an end view of a schematic representation of another embodiment of the stent shown in FIG. 1.
Figure 1:
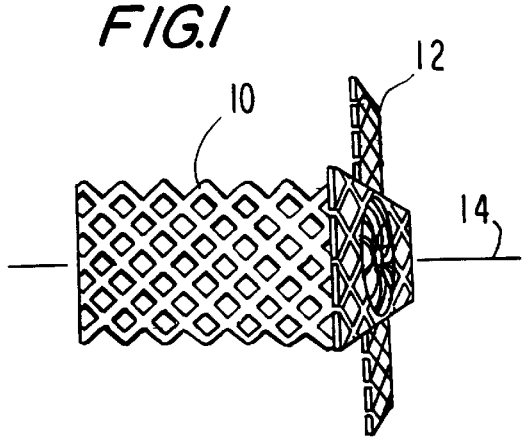
FIG. 1 depicts a perspective view of a schematic representation of a preferred embodiment of the stent of the invention showing the flared members at one end in the extended position.
Figure 2:
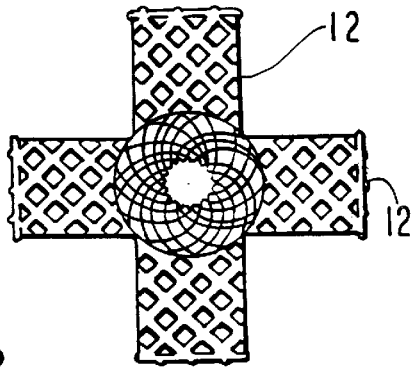
FIG. 2 depicts an end view of a schematic representation of the stent shown in FIG. 1.

The invention can perhaps be better appreciated from the drawings. FIG. 1 is a perspective view of a schematic representation of a preferred embodiment of the invention which depicts the stent 10 in an extended position showing the flared members 12 at right angles to the longitudinal axis of the tubular stent body 14. FIG. 2 depicts an end view of the stent shown in FIG. 1, where the extended flared members 12 are depicted as being of equal length and dimension at right angles to the elongated tubular stent body. The stent depicted in FIG. 2A represents another embodiment of the invention, wherein the extended flared members are not all of equal length. Here, flared members 12a are each slightly longer than flared members 12b.

Figure 3:
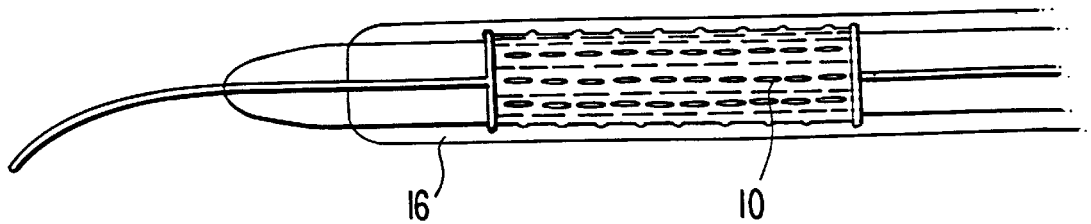
FIG. 3 depicts a schematic representation of the stent of the invention shown collapsed and constrained within a retractable sheath type delivery device.

In FIG. 3 a schematic representation of the stent 10 of the invention is shown in the collapsed position, constrained within the confines of a retractable sheath type delivery system 16. FIG. 4 depicts the stent 10 retractable sheath delivery system 16 inserted within a vessel 18 at its ostium, with the sheath portion 20 of the delivery system 16 being withdrawn after placement of stent 10.

With reference to FIGS. 5 and 6, stent 10 is depicted with the flange 12 fully extended after withdrawal of sheath 20, and is inserted firmly and securely with vessel 18.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention, which, as a matter of language, might be said to fall therebetween.

What is claimed is:

1. A stent for use in the treatment of a stenosis at the ostium of a tubular organ, comprising a tubular body capable of pressing against the stenosis to create or maintain an opening and having at one end two or more regularly spaced, substantially flat flaring members which flare to hold the stent in a secure location at said ostium, wherein the flaring members are not all of equal length.

2. The stent of claim 1 for use in the treatment of a stenosis in a blood vessel.

3. The stent of claim 1 which is fabricated out of a shape-memory material.

4. The stent of claim 1 which is fabricated out of nitinol.

5. The stent of claim 1, wherein the tubular body and the flaring members are formed from a continuous piece of material.

6. The stent of claim 1, wherein the tubular body and the flaring members are formed from two different materials.

7. The stent of claim 1, wherein the flaring members are of equal length.

8. The stent of claim 1, wherein each flaring member is capable of expanding to form an angle generally perpendicular to the longitudinal axis of the tubular body of the stent.

9. The stent of claim 1, wherein the flaring members are formed at an angle of less than 90° with reference to the longitudinal axis of the tubular body.

10. The stent of claim 1, wherein the flaring members are formed at an angle of more than 90° with reference to the longitudinal axis of the tubular body.

11. The stent of claim 1, wherein the tubular body and the flaring members are formed from a single continuous piece of material, the tubular body is self-expandable, and the flaring members are self-flaring.

12. A combination comprising a stent according to claim 1 and a retractable sheath-type delivery system.

13. A stent for use in the treatment of a stenosis at the ostium of a tubular organ, comprising a tubular body capable of pressing against the stenosis to create or maintain an opening and having at one end two or more regularly spaced, substantially flat flaring members which flare to hold the stent in a secure location at said ostium, wherein the flaring members are formed by incisions in the tubular body.

14. The stent of claim 1, wherein each flat flaring member flares outwardly to form an angle generally perpendicular to the longitudinal axis of the tubular body of the stent to hold the stent in a secure location at said ostium.

\* \* \* \* \*